United States Patent [19]

Caillouette

[11] Patent Number: 5,556,401
[45] Date of Patent: Sep. 17, 1996

[54] UTERUS MANEUVERING AND ASSOCIATED APPARATUS AND METHOD, WITH CONTROLLED DRIVE

[76] Inventor: James C. Caillouette, 685 Oak Knoll Cir., Pasadena, Calif. 91106

[21] Appl. No.: 504,899

[22] Filed: Jul. 20, 1995

Related U.S. Application Data

[63] Continuation-in-part of Ser. No. 447,347, May 23, 1995.

[51] Int. Cl.$^6$ ................................................ A61B 17/42
[52] U.S. Cl. ............................ 606/119; 606/193; 606/1; 604/55
[58] Field of Search ........................... 606/119, 193, 606/1; 604/55

[56] References Cited

U.S. PATENT DOCUMENTS

| | | |
|---|---|---|
| 3,861,380 | 1/1975 | Chassagne et al. . |
| 4,000,743 | 1/1977 | Weaver . |
| 4,085,756 | 4/1978 | Weaver . |
| 4,289,996 | 9/1981 | Barnes et al. .................. 318/38 |
| 4,430,076 | 2/1984 | Harris . |
| 4,703,241 | 10/1987 | Suzuki et al. ................. 318/599 |
| 4,775,362 | 10/1988 | Kronner . |
| 4,883,057 | 11/1989 | Broderick . |
| 4,929,949 | 5/1990 | Yamamoto et al. .............. 341/176 |
| 5,150,027 | 9/1992 | Suzuki .......................... 318/581 |
| 5,190,538 | 3/1993 | Hussein et al. . |
| 5,209,754 | 5/1993 | Ahluwalia . |
| 5,237,985 | 8/1993 | Hodgson et al. . |
| 5,282,821 | 2/1994 | Donahue ........................ 606/170 |
| 5,382,252 | 1/1995 | Failla et al. . |
| 5,395,391 | 3/1995 | Essig et al. . |
| 5,409,496 | 4/1995 | Rowden et al. . |

*Primary Examiner*—Robert A. Hafer
*Assistant Examiner*—Benjamin Koo
*Attorney, Agent, or Firm*—William W. Haefliger

[57] ABSTRACT

A uterus maneuvering apparatus comprising a lengthwise elongated boom, and a strut carried at one end of the boom to be pivoted relative to the boom, the strut and boom adapted to be inserted via the vaginal canal to locate the strut to project in the uterine cavity; actuator structure associated with the boom and strut for effecting controlled pivoting of the strut and worm gear mechanism through which drive to effect said pivoting is effected. Control structure may be provided for controlling the actuator structure, and including a servo system having an extra-corporeal manual control structure, for coupling between the manual control structure and actuator structure, the coupling including electrical signal transmission structure.

57 Claims, 4 Drawing Sheets

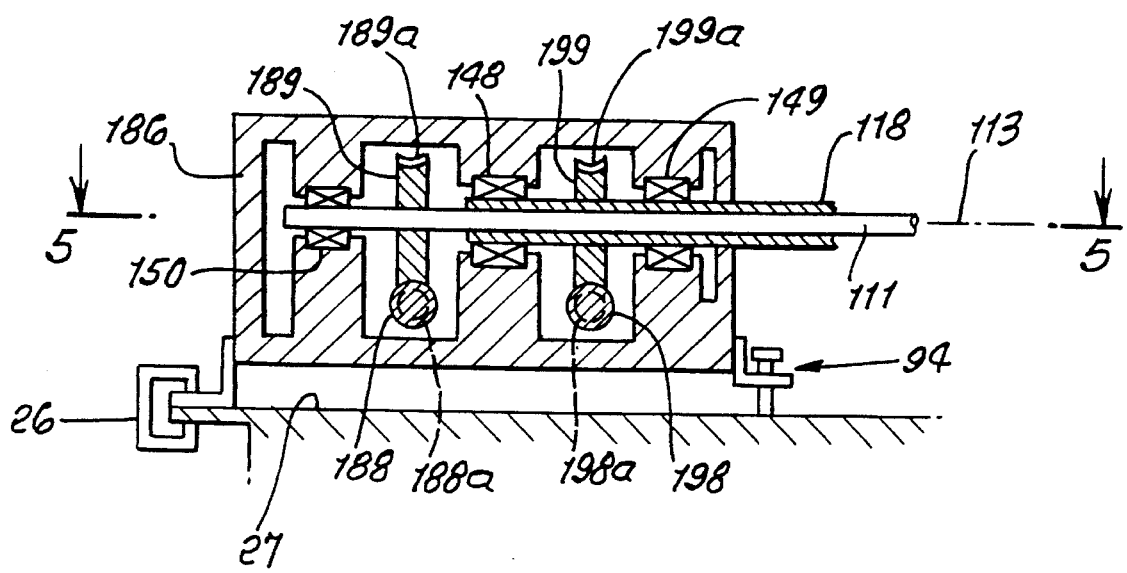
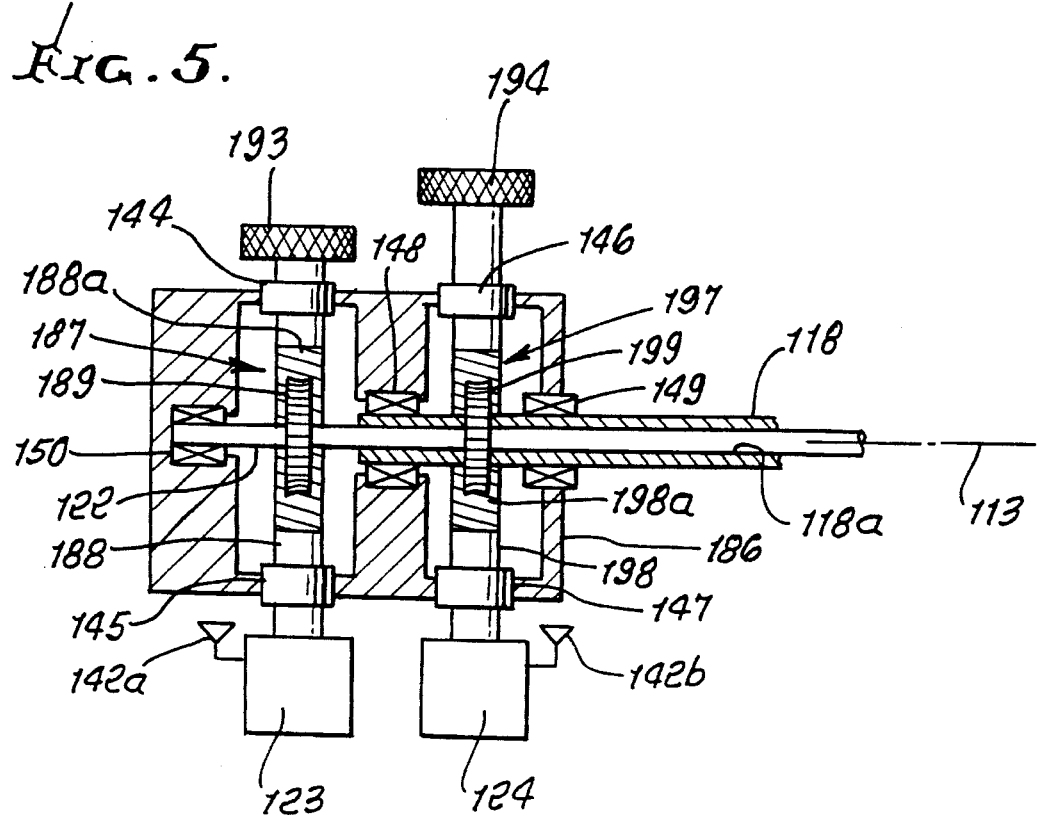

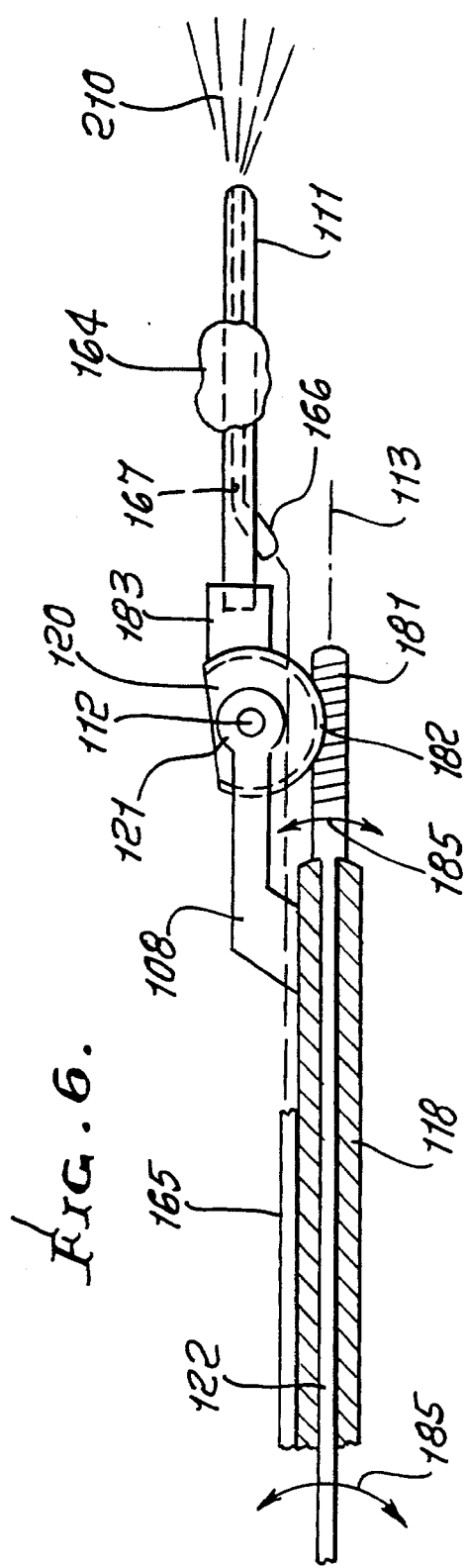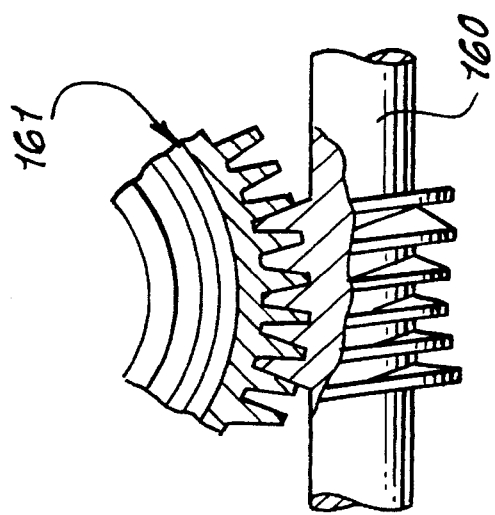

5,556,401

UTERUS MANEUVERING AND ASSOCIATED APPARATUS AND METHOD, WITH CONTROLLED DRIVE

This application is a continuation-in-part of prior U.S. application Ser. No. 08/447,347 filed May 23, 1995.

BACKGROUND OF THE INVENTION

This invention relates generally to uterus maneuvering apparatus and method, and more particularly, to automatically controllable apparatus responsive to remote control means to manipulate or maneuver a uterus, and method for effecting such remote control. Associated means to inject fluid into the uterus and oviducts, is or may be provided.

Manipulation or maneuvering of the uterus is desired, as during laparoscopic examination. In the past, mechanical devices were used for this purpose, and employed handles and triggers that were manually operated immediately outside the patient's body, the actual manipulation tip having been inserted via the vagina and cervix. This required an assistant or nurse to manually manipulate the instrument, while receiving oral instructions from the surgeon in operating position over the patient's abdomen.

There is need for improved apparatus and method of use thereof, whereby the surgeon can himself/herself directly manipulate the instrument, to maneuver the uterus, while he/she stands in operating position, and while he/she can observe the uterus position, as via an observation screen. There is also need for associated apparatus to inject fluid (for treatment, examination or identification) into the uterus and oviducts.

SUMMARY OF THE INVENTION

It is a major object of the invention to provide improved uterine maneuvering apparatus and method meeting the above need. Basically, the apparatus of the invention comprises, in combination:

a) a lengthwise elongated boom, and a strut carried at one end of the boom to be pivoted relative to the boom, the strut and boom adapted to be inserted via the vaginal canal to locate the strut to project in the uterine cavity, b) actuator means associated with the boom and strut for effecting controlled pivoting of the strut, and c) control means for controlling the actuator means, and including a servo system having an extra-corporeal manual control means, for coupling between the manual control means and actuator means, the coupling including electrical signal transmission means.

Accordingly, the surgeon may himself operate the control means, as for example via a joystick, to maneuver the uterus.

It is another object of the invention to provide such coupling between the manual control means and the actuator means, as for example in the form of a radio signal transmission link, or electrical wiring.

A further object includes the provision of support structure for the boom to orient the boom in selected position with the strut inserted into the uterus for pivoting therein; such support structure may typically carry the boom for pivoting about an axis extending lengthwise at the boom.

An additional object includes the provision of actuator means associated with the boom and strut for effecting controlled pivoting of one of the following:

i) the strut relative to the boom, ii) the boom about an axis of lengthwise elongation, iii) the strut about a first axis to the boom about a second axis, the axes being relatively perpendicular, and the actuator means including worm gear mechanism through which the controlled pivoting is effected.

Yet another object includes the provision of the actuator means to include:

i) a first electrically responsive actuator to affect pivoting of the strut about a first axis, through a first section of the worm gear mechanism, and ii) a second electrically responsive actuator to effect pivoting of the boom about a second axis, and through a second section of the worm gear mechanism.

Also, manual override controls may be employed in conjunction with such actuators.

Further objects include the provision of first manual control means movable to effect servo-controlled operation of the first actuator; and second manual control means to effect servo-controlled operation of the second actuator. Such controls may take the form of at least one joystick which the surgeon can operate at a location outside the patient's body, and remotely from the boom and strut instrumentation. In addition, auxiliary means may be employed, including an inflatable balloon carried by the strut to be remotely controllably inflated; and a fluid injection duct may extend along the boom, for remotely controllable injection into the uterus or oviducts, of fluid, as referred to above.

These and other objects and advantages of the invention, as well as the details of an illustrative embodiment, will be more fully understood from the following specification and drawings, in which:

DRAWING DESCRIPTION

FIG. 4 is a section taken through a modified form of the apparatus, employing worm gear mechanism;

FIG. 5 is a section taken on lines 5—5 of FIG. 4;

FIG. 6 is an elevation, partly in section, showing strut and strut drive mechanism, associated with the FIG. 4 and FIG. 5 modifications; and FIG. 7 is a fragmentary view of a worm drive.

DETAILED DESCRIPTION

Figure 1:
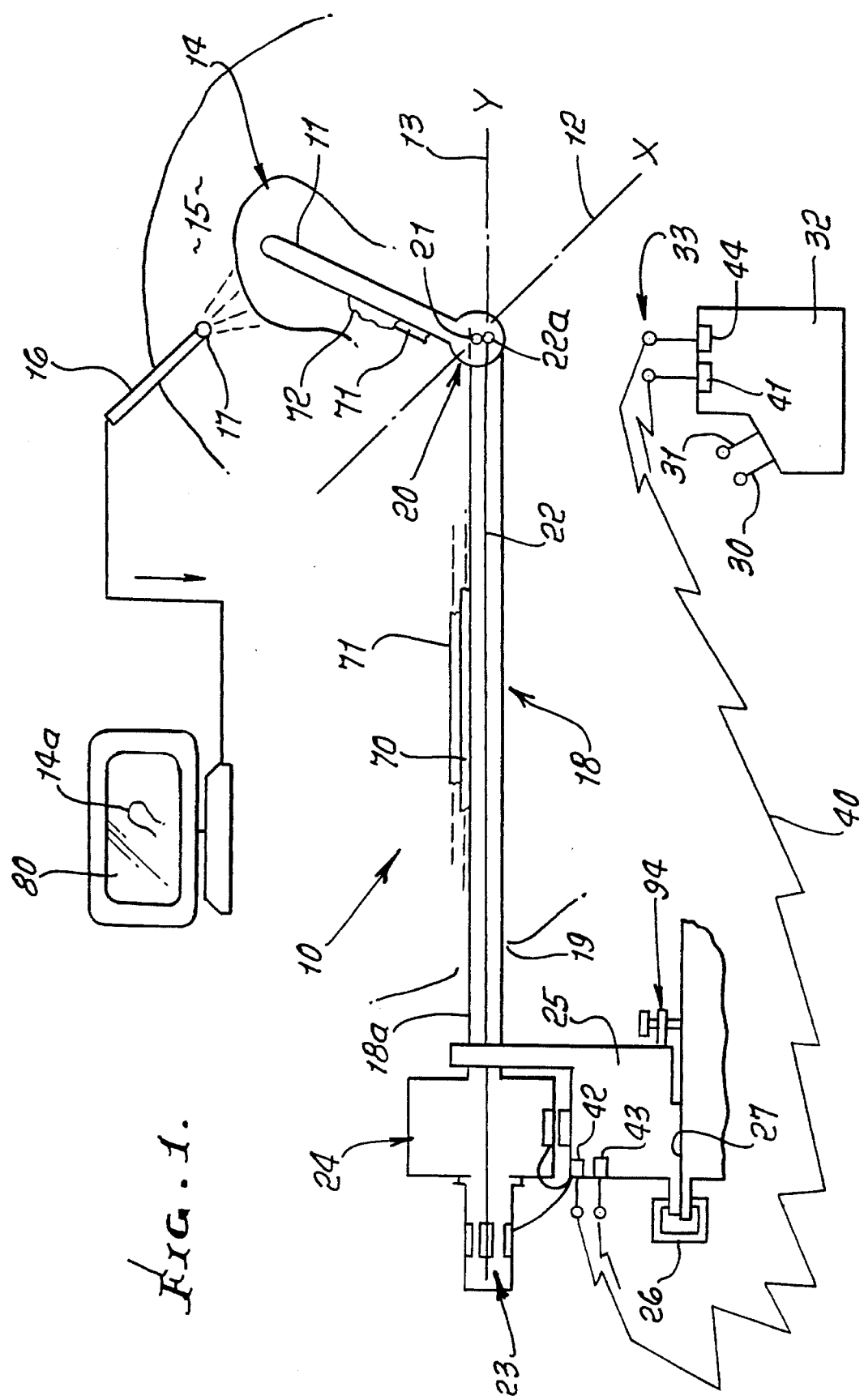
FIG. 1 is a schematic representation of a system in which the invention is embodied.

In FIG. 1, the instrument 10 includes a tip in the form of a strut 11 movable about two axes 12 and 13 (X and Y axes) for maneuvering the uterus 14 into which it has been inserted. The patient's abdominal cavity is seen at 15, and a laparoscope 16 projects into that cavity. A light source 17, on or associated with the laparoscope, illuminates the pelvic organs. The surgeon or physician normally stands adjacent the patient to look downwardly toward 16 and 17; and he/she is, therefore, at a distance, or remote from, the end 18a of the longitudinally elongated, narrow housing or boom 18 of the uterine manipulator projecting into and from the vaginal entrance 19.

Boom 18 supports strut 11, for rotation about axes 12 and 13; and merely as illustrative, a rotor 20 is pinned at 21 to the end of the boom to pivot about X axis 12, and one end of the strut 11 is connected to the rotor to rotate therewith.

An elongated actuator member 22 is connected with the rotor at 22a, in offset relation to 21, i.e., to "crank" the rotor 20 about axis 12, as member 22 is moved longitudinally endwise. A linear actuator 23 is connected to member 22, at the end of the instrument outside the patient's body. Actuator 23 is in turn carried by the rotary actuator 24 supported for rotation by a base 25. The latter is adjustably fixed in position by a clamp 26 or other means holding base 25 to a table 27. Other devices to support actuator 24 for rotation about axis 13 may be employed.

Actuator 24 is connected to the boom 18 to support it for rotation about axis 13, as actuator 24 controllably rotates, clockwise or counterclockwise, about Y axis 13.

FIG. 1 shows two joysticks 30 and 31 supported on a carrier 32, as at the location of the physician. The two joysticks are pivotally supported, as at 30a and 31a, and are pivotable to control the strut rotation about X axis 12, (i.e., up and down) and boom rotation about Y axis 13.

A servo system is provided, as indicated at 33, for coupling between the manual control means (i.e., joysticks 30 and 31, for example) and the actuator means (i.e., 23 and 24, for example). The coupling includes electrical signal transmission means, indicated at 40, in the form of a radio signal transmission link.

Radio transmitter 41, at the manual control location, and receiver 42, at the location of the actuators, transmits position control signals or data for reception at the actuators, to position the latter. AM or FM may be used, such transmission and reception circuitry being known. A feedback signal transmitter 43 at the location of the actuators transmits feedback signals for reception by a receiver 44 at the location of the control joysticks.

Figure 3:
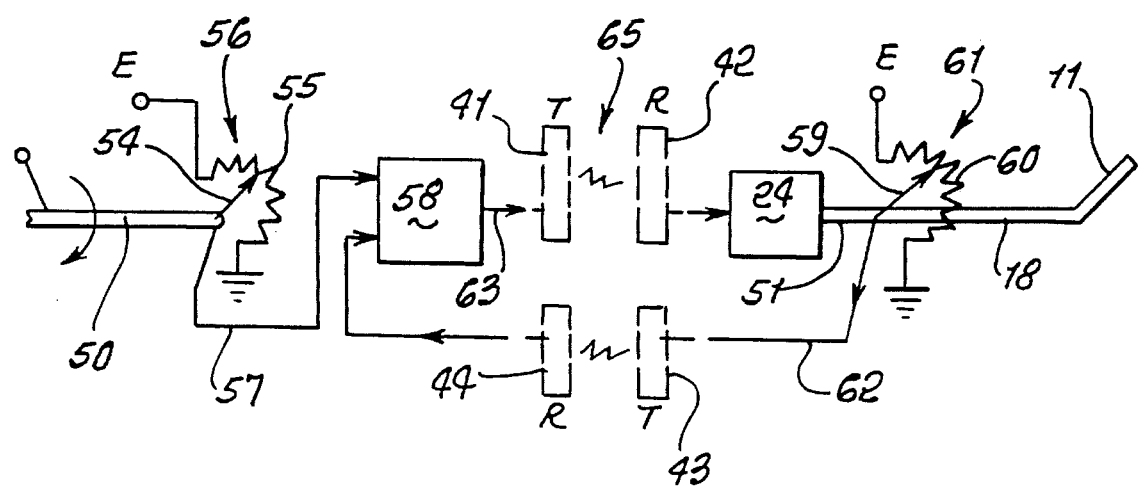
FIG. 3 is a simplified schematic drawing of a servo system.

FIG. 3 shows one basic form of an analog servo system, with a joystick-controlled input shaft 50, and an output-controlled shaft 51 (rotary or linear actuator), which corresponds to the output member of the actuator 23 or 24. A wiper 54 on the shaft 50 variably engages a resistance 55 of a potentiometer 56, to derive a position control signal on lead 57 fed to comparator 58. Similarly, a wiper 59 on the actuator output shaft 51 is moved by the latter to variably engage a resistance 60 of a potentiometer 61, to derive a shaft position-determined feedback signal on the feedback loop 62, and also fed to the comparator 58. The differencing output of the latter is transmitted at 63 to the actuator 24 to drive it forward or backward until the controlled position of shaft 51 (i.e., of boom 18) corresponds to the controlling position of the joystick. The radio communication link, including circuitry, is indicated at 65.

A similar servo is provided for the second joystick controlling the position of the actuator 23 that angularly positions the strut 11 in the uterus. Suitable DC amplification may be provided in association with the actuators to drive step-motors, or pulse motors, associated with such actuators in response to control signal reception.

The radio link at 65 may be replaced by elongated, flexible wires that extend to the actuators 23 and 24, from the comparator; and in that event, a DC amplifier may be associated with the comparator. Analog or digital servo systems may be employed.

FIG. 1 also shows a duct 70 extending along the boom 18 for controllably conducting examination or treatment fluid to the uterus. For example, a colored fluid (such as methylene blue, in saline aqueous solution) can be injected for observation. Similarly, an inflation air duct 71 may extend along the boom 18 for controllably conducting such air or gas to a balloon 72 at the middle of the strut, to be inflated in the uterus, as may be desired, for example to hold the apparatus element 11 positioned in the uterine cavity.

A CRT screen is shown at 80 to display the output of the laparoscope 16, i.e., showing the position of the uterus; and the surgeon may merely operate the joysticks to maneuver the uterus to desired position, as displayed at 14a on the screen. Scope 16 typically includes fiber optical elements, connected to the CRT or its circuitry.

Figure 2:
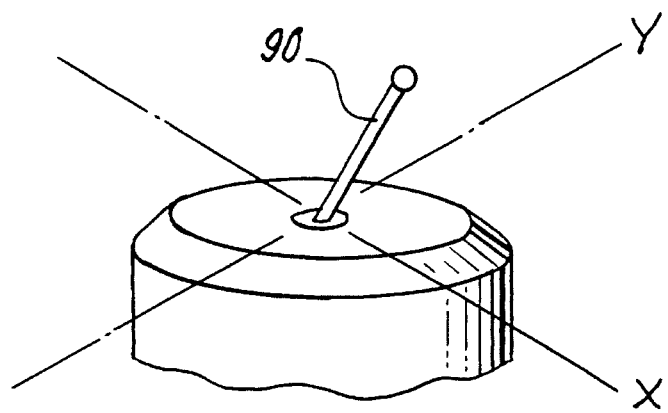
FIG. 2 is a representation of a single joystick rotatable about two axes.

FIG. 2 shows a single joystick 90 replacing the dual joysticks 30 and 31, to simplify operation and control. Joystick 90 rotates about dual axes indicated at X and Y, to control the two actuators. In FIG. 1, an adjustable support may be provided for base 25 to adjust along three perpendicular axes, for patient comfort. See for example adjustable jackscrew 94, to tilt the base, as for example relative to the patient undergoing examination.

A usable servo positioning control system, with radio link, is sold by Futaba Corporation of America, 4 Studebaker, Irvine, Calif. Such control systems are used to radio control model airplanes.

In FIG. 6, a boom 118 supports strut 111 for rotation about X axis 112 and Y axis 113. Axis 113 is defined by boom 118, the boom carrying the strut and being itself rotatable about axis 113. See arrows 185. A rotor 120 carries the strut 111 and is pivotally connected at 121 to the distal end of the boom, as via a bracket 108. An elongated rotary actuator link 122 extents within the boom 118, to rotate about axis 113 and thereby effect rotation of the rotor 120 and strut 111 about axis 112.

Worm gear elements 181 and 182 are operatively located between link 122 and the rotor to effect such controlled rotation of the strut about axis 112 and to hold or maintain the strut in angular position (relative to the boom) to which it has been rotated. See in this regard spiral thread 181 defined by the end of link 122, and gear teeth 182 on the rotor 120 and meshing with thread 181. Link 122 is rotatable clockwise and counterclockwise about axis 113, to rotate strut 111 clockwise and counterclockwise about axis 112.

Referring to FIGS. 4 and 5, an electrically responsive rotary actuator 124 is carried by the housing or frame 186; and a worm gear drive 197 is coupled between 124 and the rotary boom 118. Drive 197 includes a shaft 198 rotated by actuator or motor 124, spiral worm thread 198a on shaft 198, worm gear 199 on boom 118 extents within the housing, and gear teeth 199a on 199 and meshing with worm thread 198a. A knob 194 on shaft 198 extends at the housing exterior, to be grasped and rotated manually, to controllably rotate shaft 198 and override the motor 124, if and when desired.

Actuator means is associated with the strut 111 (as via rotary link 122) for effecting controlled pivoting thereof, as referred to. The actuator means preferably includes worm gear mechanism through which such controlled pivoting is effected, and to selected "held" position about axes 112 and 113. See in this regard the provision of an electrically responsive actuator 123 carried by housing or frame 186, and a worm gear drive 187 coupled between 123 and the rotary link 122, such as a shaft extending within the housing.

Drive 187 includes a shaft 188 rotated by rotary actuator or motor 123, spiral worm thread 188a on shaft 188, worm gear 189 on link 122 extents within the housing, and gear teeth 189a on 189 and meshing with worm thread 188a. A knob 193 on shaft 188 extends at the exterior of the housing, to be grasped and rotated manually to controllably rotate shaft 188 and override the motor 123, if and when desired.

FIG. 7 shows the worm and gear elements 160 and 161 of a worm gear drive in greater detail.

An inflatable balloon 164 is carried by the strut, as also referred to above. Also, treatment liquid may be supplied to the end of the strut for dispensing, as at 210, via duct 165 on the boom and coupled at 166 to the strut to flow within a strut passage 167.

Overrides 193 and 194 may be operated if the motors 123 and 124 are deactivated, or otherwise fail, or if joystick control of the motor, as described above in conjunction with drives 123 and 124 is insufficient for any reason. Note radio antennae 142a and 142b associated with the motors and corresponding to 42 described above.

Bearings for the shafts 188 and 198 are indicated at 144–147. Bearing supports for the boom 118 are seen at 148 and 149. A bearing support for link 122 is seen at 150. The link also has rotary support at the bore 118a of the boom. The servo control system of FIGS. 1–3 is applicable to FIGS. 4–7.

Strut 111 may have removable connection at 183 with the rotor 120, enabling attachment of a new strut to the rotor each time the apparatus is to be used.

A device, such as a clamp 26, is usable to hold the housing 186 at a selected angle relative to horizontal, as on table 27, for application of the boom and strut to a patient. See also set height adjustment at 94.

I claim:

1. In a uterus maneuvering apparatus, the combination comprising:
   a) a lengthwise elongated boom, and a strut carried at one end of the boom to be pivoted relative to the boom, the strut and boom adapted to be inserted via the vaginal canal to locate the strut to project into the uterine cavity,
   b) actuator means associated with the boom and strut for effecting controlled pivoting of the strut about a first axis and the boom about a second axis, said axes being relatively perpendicular,
   c) said actuator means including worm gear mechanism through which said controlled pivoting is effected,
   d) control means for controlling said actuator means, and including a servo system having an extra-corporeal manual control means, for coupling between said manual control means and actuator means, said coupling including electrical signal transmission means,
   e) said actuator means including:
      i) a first electrically responsive actuator to affect pivoting of the strut about said first axis, through a first section of said worm gear mechanism, and
      ii) a second electrically responsive actuator to effect pivoting of the boom, about said second axis, through a second section of said worm gear mechanism,
   f) and including a rotary link extending within the boom and coupling between the first actuator and said strut.

2. The combination of claim 1 wherein said coupling includes a radio signal transmission link.

3. The combination of claim 1 wherein said coupling includes electrical wiring.

4. The combination of claim 1 including a support structure for said boom to orient the boom in selected position with said strut inserted into the uterus for pivoting therein.

5. The combination of claim 1 wherein said worm gear mechanism includes worm gear elements located between the strut and said rotary link.

6. The combination of claim 5 wherein said support structure includes a support housing from which the boom extends, and a support stand for said housing, said support stand adapted to be anchored.

7. The combination of claim 1 wherein the second actuator is coupled to the boom to rotate the boom and strut about said second axis.

8. The combination of claim 1 wherein said manual control means includes a first manual control movable to effect servo-controlled operation of the first actuator.

9. The combination of claim 8 wherein said manual control means includes a second manual control movable to effect servo-controlled operation of the second actuator.

10. The combination of claim 9 wherein said first and second manual controls include at least one joystick.

11. The combination of claim 1 including an inflatable balloon carried by said strut to be inflated within the uterus, for maneuvering the uterus in accordance with movement of the strut.

12. The combination of claim 11 including a duct extending along the boom and to said balloon.

13. The combination of claim 1 including a fluid injection duct extending along the boom and to the strut for injecting examination or treatment fluid into the uterus.

14. The combination of claim 1 including manual control means coupled to said boom and strut to override operation of said actuators.

15. In a uterus maneuvering method, the steps that include:
   a) providing a lengthwise elongated boom, and a strut carried at one end of the boom to be pivoted relative to the boom, and inserting the strut and boom via the vaginal cavity to locate the strut to project in the uterine cavity,
   b) providing actuator means associated with the boom and strut for transmitting drives effecting controlled pivoting of the strut and boom, and
   c) providing worm gear mechanism through which said drives are effected,
   d) said actuator means provided to include:
      i) a first electrically responsive actuator to affect pivoting of the strut about a first axis, and
      ii) a second electrically responsive actuator to effect pivoting of the boom about a second axis,
   e) and providing a rotary link extending within the boom and coupling between the first actuator and said strut.

16. The method of claim 15 including providing control means for controlling said actuator means, and including a servo system having an extra-corporeal manual control means, for coupling between said manual control means and actuator means, said coupling including electrical signal transmission means, and operating said servo system to maneuver the uterus.

17. The method of claim 15 wherein said coupling includes a radio signal transmission link, and including transmitting radio signals in response to operation of said servo system.

18. The method of claim 15 wherein said coupling includes electrical wiring, and including transmitting electrical signals via said wiring, in response to operation of said servo system.

19. The method of claim 15 including providing support structure for said boom, orienting the boom in selected position in the birth canal with said strut inserted into the uterus for pivoting therein.

20. The method of claim 15 wherein said support structure is provided to carry the boom for pivoting about an axis extending lengthwise at the boom.

21. The method of claim 19 wherein said support structure includes a support housing from which the boom extends, and a support stand for said housing, and including controllably anchoring said support stand to orient the boom in said selected position.

22. The method of claim 1 including coupling the second actuator to the boom to rotate the boom and strut about said second axis.

23. The method of claim 16 wherein said manual control means is provided to include a first manual control movable to effect servo-controlled operation of the first actuator.

24. The method of claim 23 wherein said manual control means is provided to include a second manual control movable to effect servo-controlled operation of the second actuator.

25. The method of claim 24 wherein said first and second manual controls are provided to include at least one joystick.

26. The method of claim 15 including providing an inflatable balloon carried by said strut to be inflated within the uterus, for maneuvering the uterus in accordance with movement of the strut.

27. The method of claim 24 including providing a pressurization duct extending along the boom and to said balloon.

28. The method of claim 15 including providing a fluid injection duct extending along the boom and to the strut for injecting treatment fluid into the uterus.

29. In apparatus insertible into and maneuverable within the uterus, the combination comprising:
   a) a lengthwise elongated first means insertible via the vaginal canal to locate an end portion of said means to project in the uterine cavity,
   b) actuator means associated with said first means for producing drive effecting controlled maneuvering of said end portion in the uterus, and worm gear mechanism through which said drive is effected,
   c) and control means for controlling said actuator means, and including a servo system having an extra-corporeal manual control means, for coupling between said manual control means and actuator means, said coupling including electrical signal transmission means,
   d) said first means including a boom, and there being a rotary link means at least part of which extends within the boom for coupling between said actuator means and said end portion.

30. The combination of claim 29 wherein said coupling includes a radio signal transmission link.

31. The combination of claim 29 wherein said coupling includes electrical wiring.

32. The combination of claim 29 including fluid injection means carried by said first means, for injecting fluid into the uterus.

33. In body tissue maneuvering apparatus, the combination comprising:
   a) a lengthwise elongated boom, and a strut carried at one end of the boom to be pivoted relative to the boom, the strut and boom adapted to be inserted via a body opening to locate the strut to project into a body cavity,
   b) actuator means associated with the boom and strut for effecting controlled pivoting of the strut about a first axis and the boom about a second axis, said axes being relatively perpendicular,
   c) said actuator means including worm gear mechanism through which said controlled pivoting is effected,
   d) control means for controlling said actuator means, and including a servo system having an extra-corporeal manual control means, for coupling between said manual control means and actuator means, said coupling including electrical signal transmission means,
   e) said actuator means including:
      i) a first electrically responsive actuator to affect pivoting of the strut about said first axis, through a first section of said worm gear mechanism, and
      ii) a second electrically responsive actuator to effect pivoting of the boom, about said second axis, through a second section of said worm gear mechanism,
   f) and including a rotary link extending within the boom and coupling between the first actuator and said strut.

34. The combination of claim 33 wherein said coupling includes a radio signal transmission link.

35. The combination of claim 33 including a support structure for said boom to orient the boom in selected position with said strut inserted into the cavity for pivoting therein.

36. The combination of claim 30 wherein said worm gear mechanism includes worm gear elements located between the strut and said rotary link.

37. The combination of claim 36 wherein said support structure includes a support housing from which the boom extends, and a support stand for said housing, said support stand adapted to be anchored.

38. The combination of claim 33 wherein said manual control means includes a first manual control movable to effect servo-controlled operation of the first actuator.

39. The combination of claim 38 wherein said manual control means includes a second manual control movable to effect servo-controlled operation of the second actuator.

40. The combination of claim 39 wherein said first and second manual controls include at least one joystick.

41. The combination of claim 30 including an inflatable balloon carried by said strut to be inflated within the cavity, for maneuvering body tissue in accordance with movement of the strut.

42. The combination of claim 41 including a duct extending along the boom and to said balloon.

43. The combination of claim 30 including a fluid injection duct extending along the boom and to the strut for injecting examination or treatment fluid into the cavity.

44. The combination of claim 30 including manual control means coupled to said boom and strut to override operation of said actuators.

45. In body tissue maneuvering method, the steps that include:
   a) providing a lengthwise elongated boom, and a strut carried at one end of the boom to be pivoted relative to the boom, and inserting the strut and boom via a body cavity to locate the strut to project in the cavity, the body tissue associated with the cavity,
   b) providing actuator means associated with the boom and strut for transmitting drives effecting controlled pivoting of the strut and boom, and
   c) providing worm gear mechanism through which said drives are effected,
   d) said actuator means provided to include:
      i) a first electrically responsive actuator to affect pivoting of the strut about a first axis, and
      ii) a second electrically responsive actuator to effect pivoting of the boom about a second axis,
   e) and providing a rotary link extending within the boom and coupling between the first actuator and said strut.

46. The method of claim 45 including providing control means for controlling said actuator means, and including a servo system having an extra-corporeal manual control means, for coupling between said manual control means and actuator means, said coupling including electrical signal transmission means, and operating said servo system to maneuver the body tissue.

47. The method of claim 45 wherein said coupling includes a radio signal transmission link, and including transmitting radio signals in response to operation of said servo system.

48. The method of claim 45 including providing support structure for said boom, orienting the boom in selected position in the body opening with said strut inserted into the cavity for pivoting therein.

49. The method of claim 45 wherein said support structure is provided to carry the boom for pivoting about an axis extending lengthwise at the boom.

50. The method of claim 48 wherein said support structure includes a support housing from which the boom extends, and a support stand for said housing, and including controllably anchoring said support stand to orient the boom in said selected position.

51. The method of claim 50 including coupling the second actuator to the boom to rotate the boom and strut about said second axis.

52. The method of claim 46 wherein said manual control means is provided to include a first manual control movable to effect servo-controlled operation of the first actuator.

53. The method of claim 52 wherein said manual control means is provided to include a second manual control movable to effect servo-controlled operation of the second actuator.

54. The method of claim 53 wherein said first and second manual controls are provided to include at least one joystick.

55. The method of claim 45 including providing an inflatable balloon carried by said strut to be inflated within the cavity, for maneuvering the body tissue in accordance with movement of the strut.

56. The method of claim 55 including providing a duct extending along the boom and to said balloon.

57. The method of claim 55 including providing a fluid injection duct extending along the boom and to the strut for injecting treatment fluid into the cavity.

* * * * *